US010380729B2

(12) United States Patent
Hovland et al.

(10) Patent No.: US 10,380,729 B2
(45) Date of Patent: Aug. 13, 2019

(54) METHOD FOR VISUAL INSPECTION AND LOGGING

(71) Applicant: Vision IO AS, Stavanger (NO)

(72) Inventors: Øyvind Hovland, Røyneberg (NO); André Hognestad, Randaberg (NO)

(73) Assignee: Vision IO AS, Stavanger (NO)

( * ) Notice: Subject to any disclaimer, the term of this patent is extended or adjusted under 35 U.S.C. 154(b) by 0 days.

(21) Appl. No.: 15/305,279

(22) PCT Filed: Apr. 17, 2015

(86) PCT No.: PCT/EP2015/058420
§ 371 (c)(1),
(2) Date: Oct. 19, 2016

(87) PCT Pub. No.: WO2015/162067
PCT Pub. Date: Oct. 29, 2015

(65) Prior Publication Data
US 2017/0046829 A1   Feb. 16, 2017

(30) Foreign Application Priority Data
Apr. 22, 2014   (NO) .................................. 20140517

(51) Int. Cl.
*G06T 7/00*   (2017.01)
*E21B 47/00*   (2012.01)
(Continued)

(52) U.S. Cl.
CPC ........ *G06T 7/0004* (2013.01); *E21B 47/0002* (2013.01); *G01M 3/005* (2013.01);
(Continued)

(58) Field of Classification Search
CPC . G06T 7/0004; G06T 3/0018; G06T 2200/04; G06T 2200/24;
(Continued)

(56) References Cited

U.S. PATENT DOCUMENTS

| 5,493,626 A | 2/1996 | Schultz et al. |
| 2003/0198374 A1 | 10/2003 | Hagene et al. |

(Continued)

FOREIGN PATENT DOCUMENTS

| EP | 0846840 A2 | 10/1998 |
| JP | 2000331168 A | 11/2000 |

(Continued)

OTHER PUBLICATIONS

International Search Report and Written Opinion dated May 20, 2015, for corresponding International Application No. PCT/EP2015/058420; International Filing Date: Apr. 17, 2015, consisting of 12-pages.

(Continued)

*Primary Examiner* — Tat C Chio
(74) *Attorney, Agent, or Firm* — Christopher & Weisberg, P.A.

(57) ABSTRACT

A method and an arrangement for visual inspection and logging of oil and/or gas well pipes are provided. The arrangement comprises an inspection tool arranged to record, during the visual inspection, a plurality of images by recording means comprising gat least one fisheye lens. The method comprises guiding the inspection tool in an oil and/or gas well pipe, and to record a plurality of fisheye images during the guiding.

9 Claims, 3 Drawing Sheets

Figure 1:
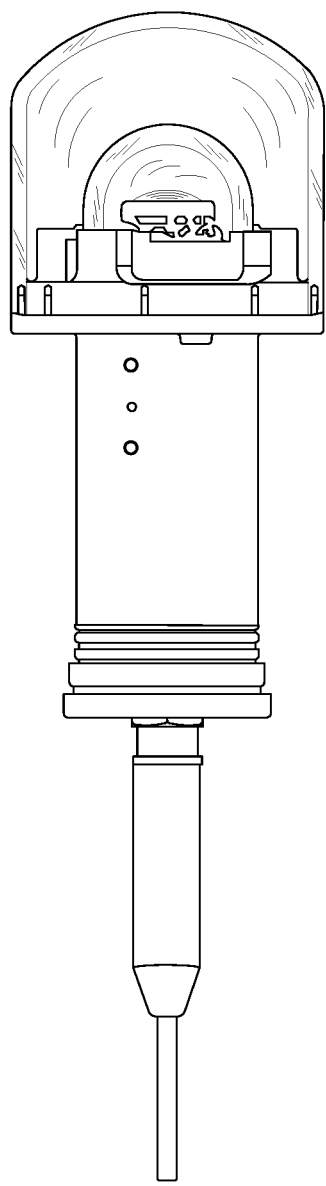

(51) Int. Cl.
   *G01M 3/00* (2006.01)
   *G02B 13/06* (2006.01)
   *G02B 23/24* (2006.01)
   *G01N 21/954* (2006.01)
   *G01V 8/12* (2006.01)
   *G06T 3/00* (2006.01)
   *H04N 5/232* (2006.01)
   *F16L 101/30* (2006.01)

(52) U.S. Cl.
   CPC ............ *G01N 21/954* (2013.01); *G01V 8/12* (2013.01); *G02B 13/06* (2013.01); *G02B 23/243* (2013.01); *G02B 23/2476* (2013.01); *G06T 3/0018* (2013.01); *H04N 5/23216* (2013.01); *H04N 5/23238* (2013.01); *F16L 2101/30* (2013.01); *G01N 2021/9542* (2013.01); *G01N 2021/9548* (2013.01); *G06T 2200/04* (2013.01); *G06T 2200/24* (2013.01); *G06T 2207/10016* (2013.01)

(58) Field of Classification Search
   CPC ............ G06T 2207/10016; G01V 8/12; H04N 5/23216; H04N 5/23238; E21B 47/0002; G01M 3/005; G02B 13/06; G02B 23/2476; G02B 23/243; F16L 2101/30; G01N 2021/9548; G01N 21/954; G01N 2021/9542
   See application file for complete search history.

(56) References Cited

U.S. PATENT DOCUMENTS

| | | |
|---|---|---|
| 2004/0021858 A1 | 2/2004 | Shima et al. |
| 2004/0211894 A1 | 10/2004 | Hother et al. |
| 2006/0290779 A1 | 12/2006 | Reverte et al. |
| 2008/0068601 A1 | 3/2008 | Thayer et al. |
| 2012/0069172 A1* | 3/2012 | Hudritsch ............ G01N 21/954 348/84 |
| 2012/0134533 A1* | 5/2012 | Del Grande ......... G06K 9/0063 382/103 |
| 2012/0192640 A1 | 8/2012 | Minh et al. |
| 2012/0257042 A1* | 10/2012 | McKaigue ........... G01N 21/954 348/84 |
| 2012/0287232 A1* | 11/2012 | Natroshvili ............... G06T 7/85 348/36 |
| 2013/0155182 A1* | 6/2013 | Bekiares ............ H04N 5/23203 348/36 |
| 2014/0056507 A1* | 2/2014 | Doyle .................. G01B 11/002 382/152 |

FOREIGN PATENT DOCUMENTS

| | | |
|---|---|---|
| JP | 2001227925 A | 8/2001 |
| JP | 2007024746 A | 2/2007 |
| JP | 2009168499 A | 7/2009 |
| JP | 2009210588 A | 9/2009 |
| WO | 2009068942 A1 | 6/2009 |

OTHER PUBLICATIONS

Norwegian Office Action dated Oct. 31, 2014, for corresponding Norwegian Application No. 20140517; Filing Date: Apr. 22, 2014 consisting of 5-pages.

Norwegian Office Action dated May 18, 2016, for corresponding Norwegian Application No. 20140517; Filing Date: Apr. 22, 2014 consisting of 6-pages.

* cited by examiner

METHOD FOR VISUAL INSPECTION AND LOGGING

CROSS-REFERENCE TO RELATED APPLICATIONS

This application is a Submission under 35 U.S.C. § 371 for U.S. National Stage Patent Application of, and claims priority to, International Application Number PCT/EP2015/058420, filed Apr. 17, 2015, entitled "A METHOD FOR VISUAL INSPECTION AND LOGGING", which is related to and claims priority to Norwegian Patent Application Number 20140517, filed Apr. 22, 2014, the entire contents of both of which are hereby incorporated herein by reference.

TECHNICAL FIELD

Embodiments herein relate to a method, a computer program and an arrangement for visual inspecting and logging of oil and/or gas well pipes.

BACKGROUND

In the drilling and production of oil and gas wells, it is often necessary to obtain inner surface information concerning conditions present within the borehole. For example, tools and other objects may become lodged in the borehole during the drilling of a well. Such objects must be retrieved before drilling can continue.

In the operation and/or periodic maintenance of producing or injection wells, it is frequently necessary to obtain information about the construction and/or operating condition of production equipment located downhole. For example, detection of the onset of corrosion damage to well tubing or casing within a borehole enables the application of anti-corrosive treatments to the well. Early treatment of corrosive well conditions prevents the highly expensive and dangerous replacement of corrosion damaged well production components.

For performing other maintenance operations in a production well environment, such as replacement of various flow control valves or the inspection of the location and condition of casing perforations, it is highly desirable for an operator located at the surface to obtain accurate, real-time information about downhole conditions.

In fact, new regulations require operators of oilfields to perform a visual inspection of their safety/barrier valves after certain operations to verify cleanness to secure a further safe operation. These are often referred to as Blow-Out Preventers (BOP) which are large, specialized valves or similar mechanical devices, usually installed redundantly in stacks, used to seal, control and monitor oil and gas wells, and intended to prevent tubing (e.g. drill pipe and well casing), tools and drilling fluid from being blown out of the wellbore (also known as borehole, the hole leading to the reservoir) when a blowout threatens.

Other tubulars may need inspection. This is the case of risers, large tubulars connecting Oil and Gas exploration or production platforms or ships to subsea installations.

Logging in environments as described above involves inserting an apparatus with sensors into the pipe and lowering it towards the oil and/or gas reservoir. The lowering means may be an installation on a platform like a winch with a wire or a free standing lowering means. The lowering means involve means for indication of the depth of the apparatus. The sensors built into the apparatus may measure temperature, pressure and/or other variables of interest. In combination with the depth these values are plotted graphically and may be compared to other graphs of an ideal or wanted case in order to evaluate the condition of the pipe. A temperature or pressure variance may indicate that something is wrong with the pipe, and the correct measures can be taken.

To improve the logging process visual inspection tools have been introduced. For example, EP0846840 describes a capsule that employs a method with both optical equipment for an end view and for a side view, which may record and send pictures of the inner surface of the pipe to an operator. The first optical equipment is positioned directly downwards while the second optical equipment is placed perpendicular to the first, facing directly to the inner wall. The tool is inserted in the pipe and is lowered as described above.

Because of the camera positions, the visual logging inspection tool described above may however not visualize the entire inside of the pipe in a continuous manner. To get a full 360/180 degree view, visual representation of the pipe wall and to ensure that no relevant area is potentially overseen, the tool have to be stopped and rotated regularly. This makes it both difficult and time consuming to inspect the inner wall of a well pipe if it is not known exactly what abnormalities to look for, and where in the well pipe to look for them. Thus, important areas of the well pipe may be overseen.

SUMMARY

It is therefore a need when it comes to inspection systems of tubular constructions for a logging system that works as recording system without requiring a visual real-time control, but that may be edited retrospectively both in terms of position, and/or time and content.

One object of the present disclosure is to reduce or ameliorate at least one of the disadvantages of the prior art systems and/or methods, or to provide a useful alternative. This object is in a first aspect achieved by a method performed by an arrangement for visual inspection of oil and/or gas well pipes. The arrangement comprises an inspection tool arranged to record, during the visual inspection, a plurality of images by recording means comprising at least one fisheye lens. The arrangement is adapted to guide the inspection tool in an oil and/or gas well pipe, and to record, by the recording means, a plurality of fisheye images of the inside surface of the pipe while guiding the recording means through the pipe.

This object is in a second aspect achieved by an arrangement for visual inspection and logging of oil and/or gas well pipes comprising an inspection tool arranged to, by recording means comprising at least one fisheye lens, record a plurality of images of the inside surface of the pipe while guiding the recording means through the pipe. The arrangement comprises guiding means adjusted to guide the inspection tool in an oil and/or gas well pipe while recording fisheye images.

FIGURES

Figure 2:
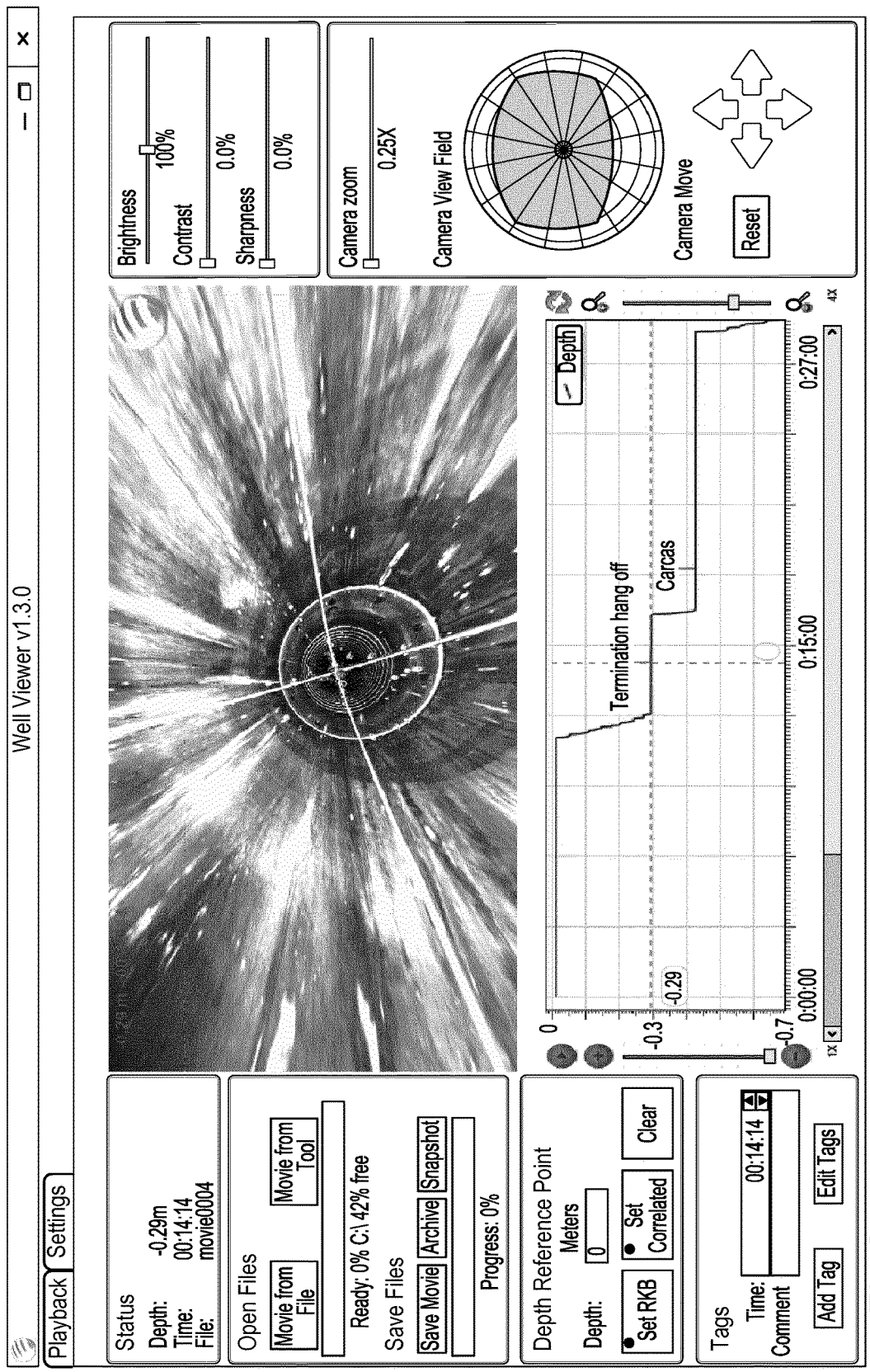
Figure 3:
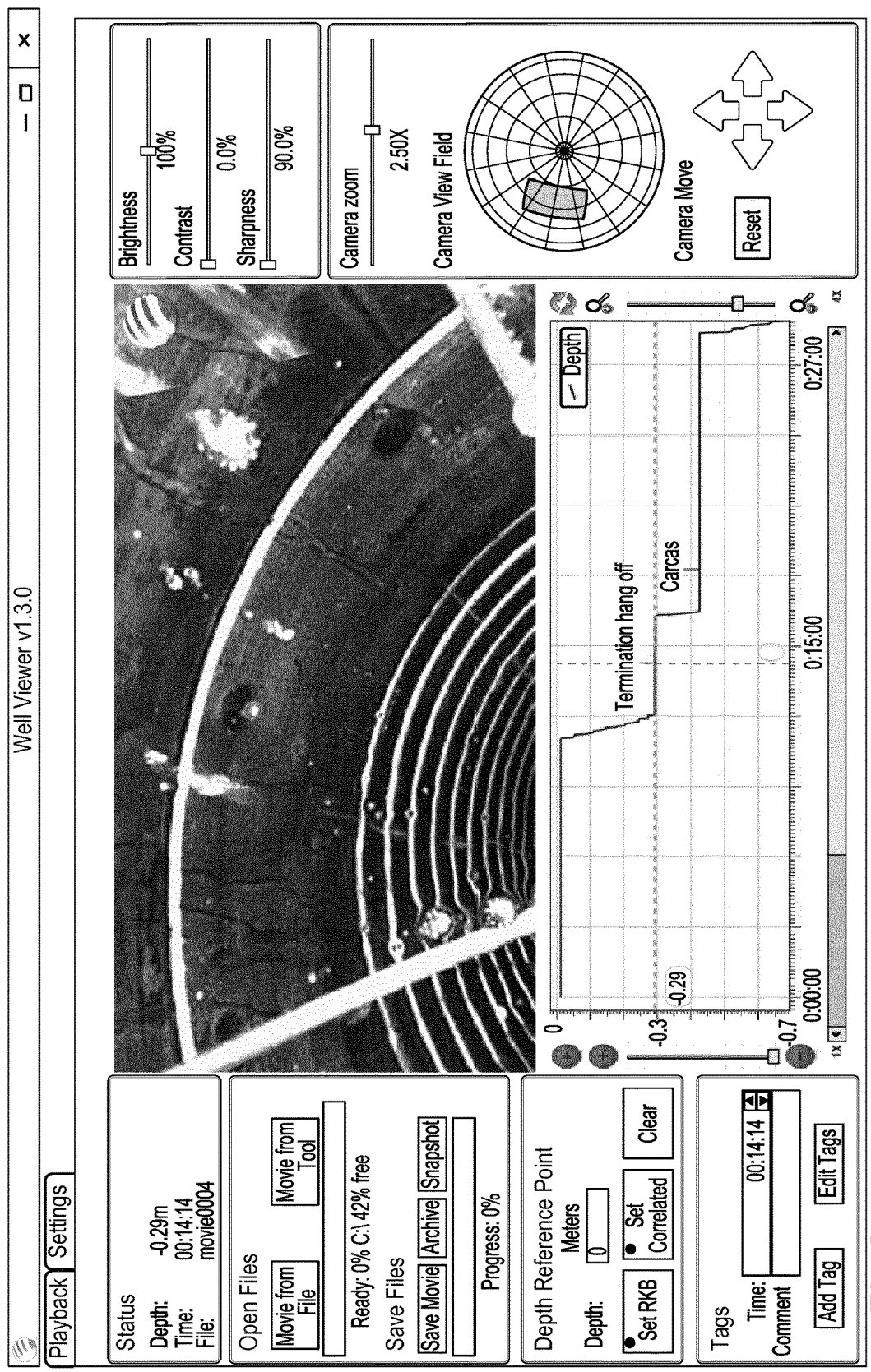

FIG. 1 illustrates an example of an inspection camera for fluid filled pipes according to state of the art, FIG. 2 is a first snap shot of a user interface monitoring a recorded well logging, FIG. 3 is a second snap shot of a user interface monitoring a recorded well logging.

DETAILED DESCRIPTION

In the following, embodiments herein will be discussed and example embodiments will be described by referring to the accompanying drawings.

An arrangement adapted to perform methods for visual inspection of oil and/or gas well pipes is provided. The arrangement comprises an inspection tool arranged to record, during the visual inspection, a plurality of images by recording means comprising at least one fisheye lens. The arrangement is adapted to guide the inspection tool in an oil and/or gas well pipe, and to record, by the recording means, a plurality of fisheye images of the inside surface of the pipe while guiding the recording means through the pipe.

Methods herein may further comprise assigning each of the recorded plurality of fisheye images a respective time stamp according to a running clock.

Methods herein may further comprise transforming the recorded plurality of fisheye images into corresponding rectilinear images, and adapt the corresponding rectilinear images for view in a graphical user interphase enabling a user to virtually move in the rectilinear images.

The transforming of the fisheye images into corresponding rectilinear images may further comprise mapping the fisheye images onto a virtual projection dome using a linear scaled mapping function, placing a virtual camera in the centre of the virtual projection dome, and generate the corresponding rectilinear images by rendering the virtual projection dome as a 3D object using GPU 3D rendering.

The user may virtually move in the rectilinear images by zooming, tilting and/or panning the virtual camera in the virtual projection dome. A sketched area in a graphical sphere of the graphical interface may indicate which part of a cross section the oil and/or gas well pipes corresponding to the virtual projection dome that is currently being viewed in the rectilinear images.

A computer program, comprising computer readable code units which when executed in an arrangement causes the arrangement to perform any of the methods described is also provided.

The embodiments herein relates to an arrangement and to methods for inspection of all kinds of fluid filled tubulars; pipes, oil- and gas wells and production- and workover risers, BOPs etc., where visual camera inspections are being performed to enhance image quality during visual camera inspection, more particularly, to a device for enabling an unobstructed optical or acoustic inspection of physical conditions within a borehole. Such inspections may be practiced e.g. during or after maintenance and servicing of oil, gas, geothermal, and injection wells.

An arrangement for visual inspection and logging of oil and/or gas well pipes is provided. The arrangement comprises an inspection tool arranged to record a plurality of images by recording means comprising at least one fisheye lens. The arrangement may further comprise an assigning means adjusted to assign each of the plurality of fisheye images to a respective time stamp according to a running clock. The arrangement may still further comprise a transforming means adjusted to transform the plurality of fisheye images into corresponding rectilinear images. The arrangement may further comprise a rectilinear means adjusted to rectilinear images to be viewed in a graphical interphase enabling a user to virtually move in the rectilinear images.

FIG. 1 illustrates an example of an inspection assembly. The inspection assembly in this example comprises a sensor 12, which in FIG. 1 is exemplified as a camera socket 14, a camera lens 16 and a lens capsule 18. Moreover, the inspection assembly 10 comprises an optical cable 20 connected to the sensor 12. In addition, there is a light source (not shown) provided to illuminate the camera's area of view.

The camera socket typically comprises hardware for sensing and processing images enclosed by a shield adjusted to protect the hardware from e.g. friction, impacts and pressure differences while running through the pipe. The camera lens may preferably be protected by a transparent lens capsule.

The arrangement comprises guiding means adjusted to guide the inspection tool in an oil and/or gas well pipe while recording, by the recording means, a plurality of fisheye images of the inside surface of the pipe while guiding the recording means through the pipe. Thus, means that may lower the capsule into the well pipe is provided. This mean may be installed on the platform or may be free standing means like a winch or tractor. The inspection tool may comprise at least one depth sensor. Methods herein may further comprise sensing the depth of the inspection tool during the moving, and assigning a respective depth to the corresponding time stamps. Methods herein may further comprise indicating depths corresponding to the respective time stamps associated with currently viewed rectilinear images in the graphical interface. Thus, the capsule lowering means may further comprise means that may give indications of the depth of the capsule. The capsule lowering means may control the capsule speed, and may stop the capsule completely if desired. As an example the speed of the capsule may not exceed 10 m/min.

The camera socket may comprise camera means in order to record or in real time to supply an observer with 360/180 degree pictures of the pipe wall. The camera means may further comprise a lens known as a "fisheye" lens. A fisheye lens as referred to herein may be an ultra-wide-angle lens that produces strong visual distortion intended to create a wide panoramic or hemispherical image. Fisheye lenses achieve extremely wide angles of view by forgoing producing images with straight lines of perspective (rectilinear images), opting instead for a special mapping, which gives images a characteristic convex non-rectilinear appearance. The fisheye lens may have the ability of recording pictures in 182 degrees. The camera means may take pictures continuously throughout operation. As an example, the camera may record images at a frame rate of 4-5 fps. The device may further comprise a capsule enclosing equipment and hardware. The capsule may be built of a heat isolating material that may withstand the environment in the well.

A computer program may be installed on hardware and placed in the top side of the well. The computer program may further comprise an algorithm for processing the images received by the camera device in real-time. The process may comprise:

1. Mapping the fisheye image onto a virtual projection dome using a linear scaled (equidistant) mapping function.
2. Placing a virtual camera in the centre of the virtual 3D dome in order to avoid projection distortions, and using a normal rectilinear pinhole projection. The virtual camera may then project the dome into a rectangular/planar view suitable to be displayed on a flat screen.
3. Generating the output image by rendering the dome as a 3D object using GPU 3D rendering.

This digital Pan/Tilt/Zoom (PTZ) algorithm transforms a fisheye image into a rectilinear image. In this process, arbitrary pan, tilt and zoom may be applied to emulate a mechanical and optical PTZ solution without any moving parts. By using a Graphics Processing Unit (GPU) the algorithm is highly efficient and easily capable of unwarping large fisheye images in real time.

A fisheye lens distorts the image to fit what was intended to be projected on a sphere, to a disc of pixels onto a planar image sensor instead. To display the image correctly it is projected onto a hemisphere or dome using an identical lens and optical setup. A projector with a fisheye lens may thus project the image correctly onto a projection dome/spherical canvas. While this is a true 1:1 optical distortion free reproduction of the original panoramic scene, the aim of this algorithm is to display this on a flat screen. Placing a camera with a normal rectilinear lens inside the dome may enable arbitrary rotation and zoom to give different views of the original image. This algorithm achieves the same result using 3D graphics hardware to emulate that setup.

In the following, an example of an algorithm processing the images according to the above disclosed example is as follows:

A virtual projection dome/canvas may be approximated by a triangular mesh arranged in a hemispherical configuration. The fisheye image is then mapped onto this virtual projection dome using a linear scaled (equidistant) mapping function: $r = f \cdot \theta$, where r is the distance of a point from the image's center, f is the focal length of the optical system and $\theta$ is the angle from the optical axis. This function may be applied to every vertex in the triangle mesh, calculating the corresponding 2D fisheye image pixel coordinates for each 3D position. A successful mapping requires knowledge of the optical axis' image pixel coordinate as well as the lens' focal length, f, in sensor pixels.

A virtual camera may be placed in the center of the virtual 3D dome to avoid projection distortions. Using a normal rectilinear pinhole projection this camera may then project the dome into a rectangular/planar view suitable to be displayed on a flat screen. The camera may be freely rotated to view in any direction including the blind spots of the fisheye lens, which is rendered as black. The camera may also zoom by changing the pinhole projections focal length.

The output image may be generated by rendering the dome as a 3D object using GPU 3D rendering. The original fisheye image may be copied onto a GPU texture in a suitable pixel format. Using the pre-calculated 3D and 2D coordinates in the dome mesh vertices, the GPU texture filtering hardware provides the actual per-pixel remapping function by interpolating between the vertices, also known as rasterization. Given a sufficient number of triangles in the dome mesh, this interpolation is virtually error free and provides bilinear filtering for a smooth and visually pleasing result. The actual pan, tilt and zoom are thus simply controlled by the virtual camera's orientation and focal length parameters.

The computer program may further comprise means to collect depth measurements and data from the apparatus and mix this to a presentation with relevant data and pictures from the camera means for the observer. The pictures are presented as an imaginary pipe that give the observer a visual representation of the pipe wall with pictures from the pipe in real-time or for post process viewing. Relevant areas on the pipe wall seen on the images and the camera can in real time or in post processing paned, tilted or zoomed in on. The computer program may further comprise means to display the pictures as a continuous video in real time or as single frames or a continuous video in post-processing with depth and time as parameters. The computer program may further comprise means to highlight and tag relevant areas in the picture stream.

FIGS. 2 and 3 are screen snap shots of an example of a user interface when monitoring a visual logging. At the right hand side of FIGS. 2 and 3, there is a graphical sphere with a sketched area indicating which part of the current cross section of the pipe or well that is being displayed in the center view of the figure. In the case of FIG. 2, the sketched area is covering the middle area of the sphere, and the corresponding display of the current cross section area is displayed in the center view of the figure.

As shown in FIG. 2, left, right, up and down arrows are provided in addition to a "camera zoom" bar. By activating these arrows and this bar, a user can navigate in the pre-recorded and projected image of the pipe accordingly.

FIG. 3 illustrates an example where the user has navigated from the situation shown in FIG. 2 by clicking using the arrows and the zoom bar focusing on a part of the pipe wall on the left hand side. As may be seen, the sketched area of the sphere is now narrowed and moved to the left, according to the displayed image. The depth and the time is the same as in the situation in FIG. 2.

The time parameter may represent the recording time, which is editable. Provided that the virtual inspection device has been lowered and lifted through the whole of the inspection area of the pipe during a certain time period, editing this time parameter will virtually move the virtual inspection device along the pipe. The displayed depth parameter may also change accordingly. The user will then subsequent to the physical inspection be able to virtually inspect the pipe at all depths where the inspection tool has been present during the physical inspection.

The above description discloses different example embodiments for illustrative purposes. A person skilled in the art would realize a variety of sensor covers, kits and inspection assemblies within the scope of the appended claims.

The invention claimed is:

1. A method performed by an arrangement for visual inspection of a pipe, the pipe being for at least one from the group consisting of oil and gas, the arrangement comprising an inspection tool arranged to record, during the visual inspection, a plurality of images by a recording means comprising at least one fisheye lens, the method comprising:
   guiding the inspection tool in the pipe; and
   recording by the recording means a plurality of fisheye images of the inside surface of the pipe while guiding the recording means through the pipe;
   transforming the recorded plurality of fisheye images into corresponding rectilinear images by:
      mapping the fisheye images onto a virtual projection dome using a linear scaled mapping function;
      placing a virtual camera in the center of the virtual projection dome;
      applying, by the virtual camera, a rectilinear pinhole projection to project the virtual projection dome into a planar view; and
      generating the corresponding rectilinear images based at least in part on the application of the rectilinear pinhole projection and a rendering of the virtual projection dome as a 3D object using GPU 3D rendering; and
   adapting the corresponding rectilinear images for view in a graphical user interface enabling a user to virtually move in the rectilinear images.

2. The method according to claim 1, further comprising assigning each of the recorded plurality of fisheye images a respective time stamp according to a running clock.

3. The method according to claim 2, the inspection tool including at least one depth sensor, the method further comprising:

sensing the depth of the inspection tool during the moving; and assigning a respective depth to the corresponding time stamps.

4. The method according to claim 3, further comprising indicating depths corresponding to the respective time stamps associated with currently viewed rectilinear images in the graphical interface.

5. The method according to claim 1, wherein the user is enabled to virtually move in the rectilinear images for at least one from the group consisting of zooming, tilting and panning the virtual camera in the virtual projection dome.

6. The method according to claim 1, wherein a sketched area in a graphical sphere of the graphical interface is indicating which part of a cross section of the pipe corresponding to the virtual projection dome is currently being viewed in the rectilinear images.

7. A system for visual inspection and logging of a pipe, the pipe being for at least one from the group consisting of oil and gas, the system comprising:

an inspection tool arranged to record a plurality of images by recording means comprising at least one fisheye lens;

guiding means adjusted to guide the inspection tool in the pipe while recording, by the recording means, a plurality of fisheye images of the inside surface of the pipe while guiding the recording means through the pipe; and transforming means adjusted to transform the recorded plurality of fisheye images into corresponding rectilinear images by:

mapping the fisheye images onto a virtual projection dome using a linear scaled mapping function;

placing a virtual camera in the center of the virtual projection dome;

applying, by the virtual camera, a rectilinear pinhole projection to project the virtual projection dome into a planar view; and generating the corresponding rectilinear images based at least in part on the application of the rectilinear pinhole projection and a rendering of the virtual projection dome as a 3D object using GPU 3D rendering; and rectilinear means adjusted to adapt the corresponding rectilinear images for view in a graphical user interface enabling a user to virtually move in the rectilinear images.

8. The system according to claim 7, further comprising an assigning means adjusted to assign each of the plurality of fisheye images to a respective time stamp according to a running clock.

9. A computer hardware including computer readable code units which when executed to by the computer hardware, causes the computer hardware to perform the method according to claim 1.

* * * * *